US005186176A

United States Patent [19]
Hiki et al.

[11] Patent Number: 5,186,176
[45] Date of Patent: Feb. 16, 1993

[54] ULTRASONIC DIAGNOSIS APPARATUS

[75] Inventors: Susumu Hiki, Ootawara; Takashi Yanagawa; Isao Uchiumi, both of Tochigi, all of Japan

[73] Assignee: Kabushiki Kaisha Toshiba, Kawasaki, Japan

[21] Appl. No.: 682,375

[22] Filed: Apr. 9, 1991

[30] Foreign Application Priority Data

Apr. 11, 1990 [JP] Japan .................................... 2-95280
Mar. 15, 1991 [JP] Japan .................................... 3-51362

[51] Int. Cl.⁵ .............................................. A61B 8/12
[52] U.S. Cl. .......................... 128/661.01; 128/660.04; 128/660.05; 128/662.03
[58] Field of Search ...................... 128/660.04, 660.05, 128/660.07, 660.1, 661.01, 662.03; 73/861.25, 628

[56] References Cited

U.S. PATENT DOCUMENTS

| | | | |
|---|---|---|---|
| 4,416,286 | 11/1983 | Iinuma et al. ................ | 128/661.01 |
| 4,630,612 | 12/1986 | Uchida et al. ................ | 128/660.05 |
| 4,830,015 | 5/1989 | Okazaki ......................... | 128/660.04 |
| 4,913,159 | 4/1990 | Gardin et al. ................. | 128/661.1 |
| 5,040,537 | 8/1991 | Katakura ...................... | 128/662.02 |

Primary Examiner—Kyle L. Howell
Assistant Examiner—George Manuel
Attorney, Agent, or Firm—Finnegan, Henderson, Farabow, Garrett and Dunnar

[57] ABSTRACT

An ultrasonic diagnosis apparatus comprises an ultrasonic probe like a biplane probe having two ultrasonic transducers, a switch for selecting one of the ultrasonic transducers, a transmitting-receiving system for driving an ultrasonic transducer selected by the switch to transmit and receive ultrasonic waves, a B-mode image producing means responsive to a receive signal from the ultrasonic transducer driven by the transmitting-receiving system for producing an ultrasonic cross-sectional image, a scanning-plane mark generator for generating a scanning-plane mark indicating the positional relationship between the ultrasonic scanning plane formed by the ultrasonic transducer selected by the switch and the other ultrasonic scanning plane formed by the other ultrasonic transducer and a TV monitor for displaying a superimposition image in which the scanning-plane mark generated by the scanning-plane mark generator is superimposed on the ultrasonic cross-sectional image produced by the B-mode image producing system.

29 Claims, 21 Drawing Sheets

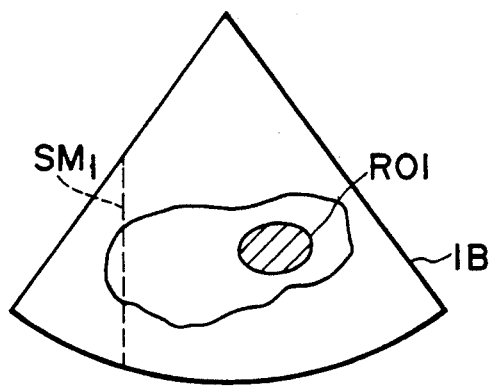
F I G. 7A
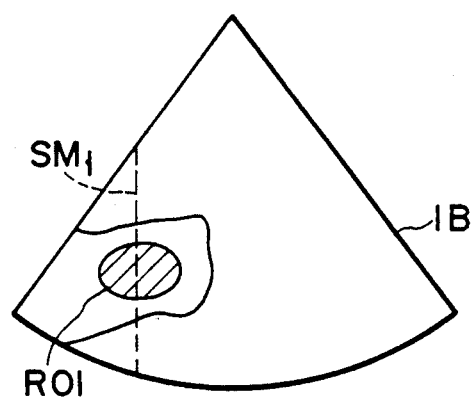
F I G. 7B
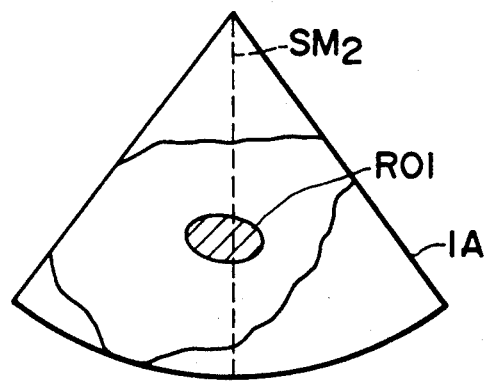
F I G. 7C

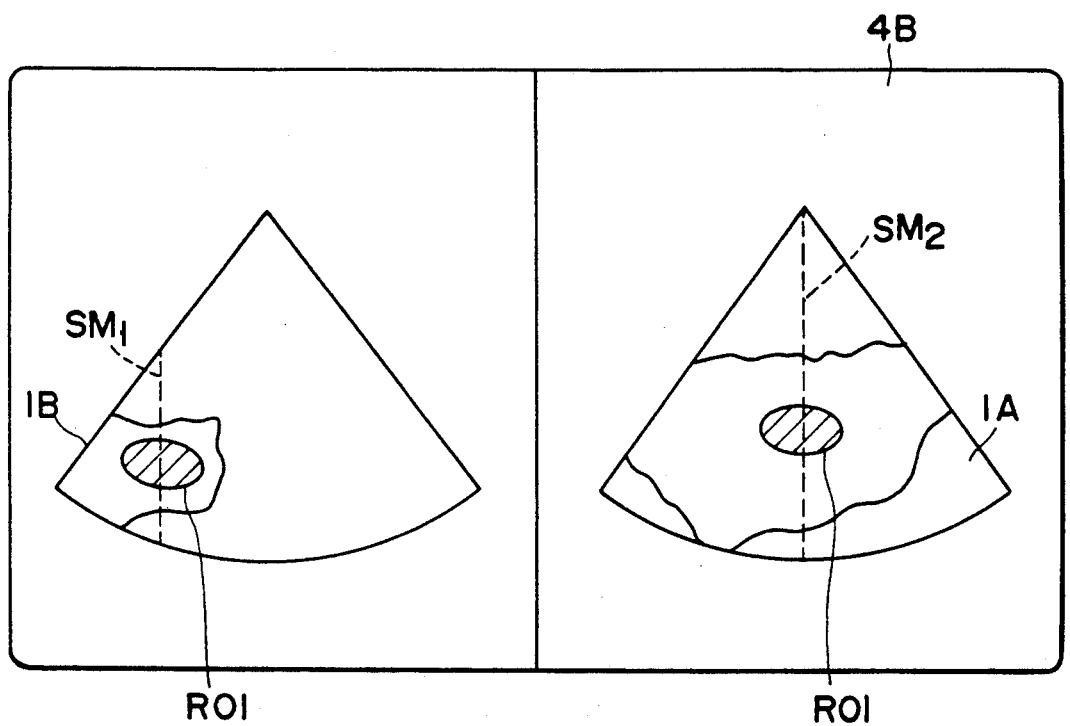
F I G. 8

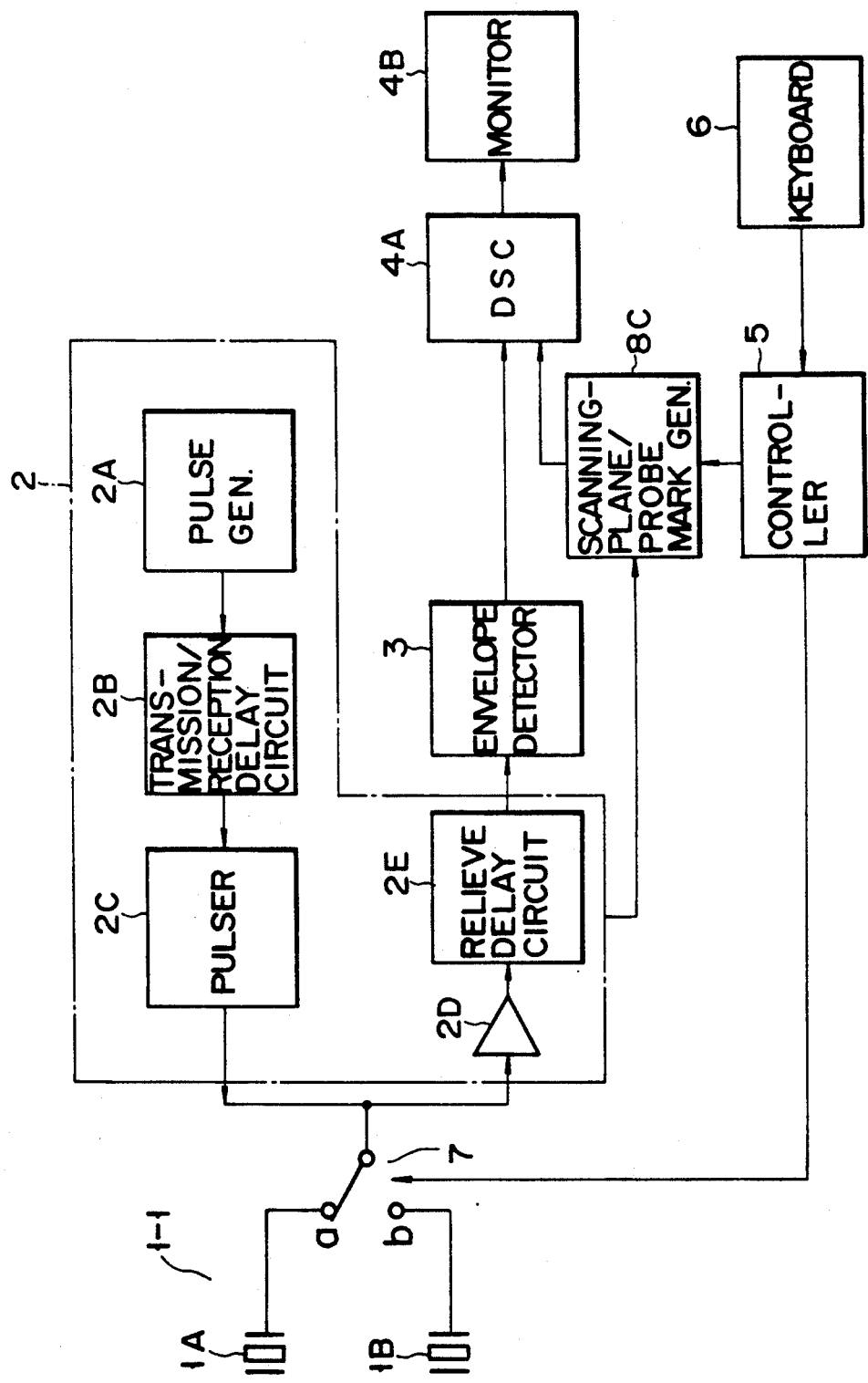
F I G. 12

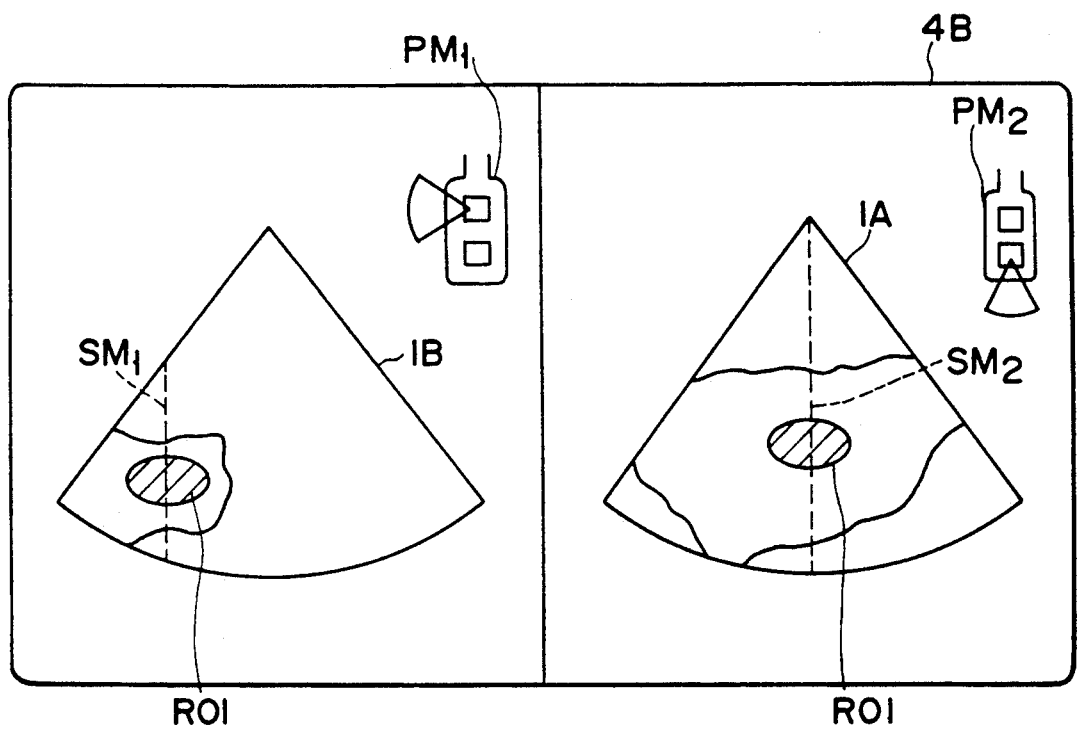
F I G. 13

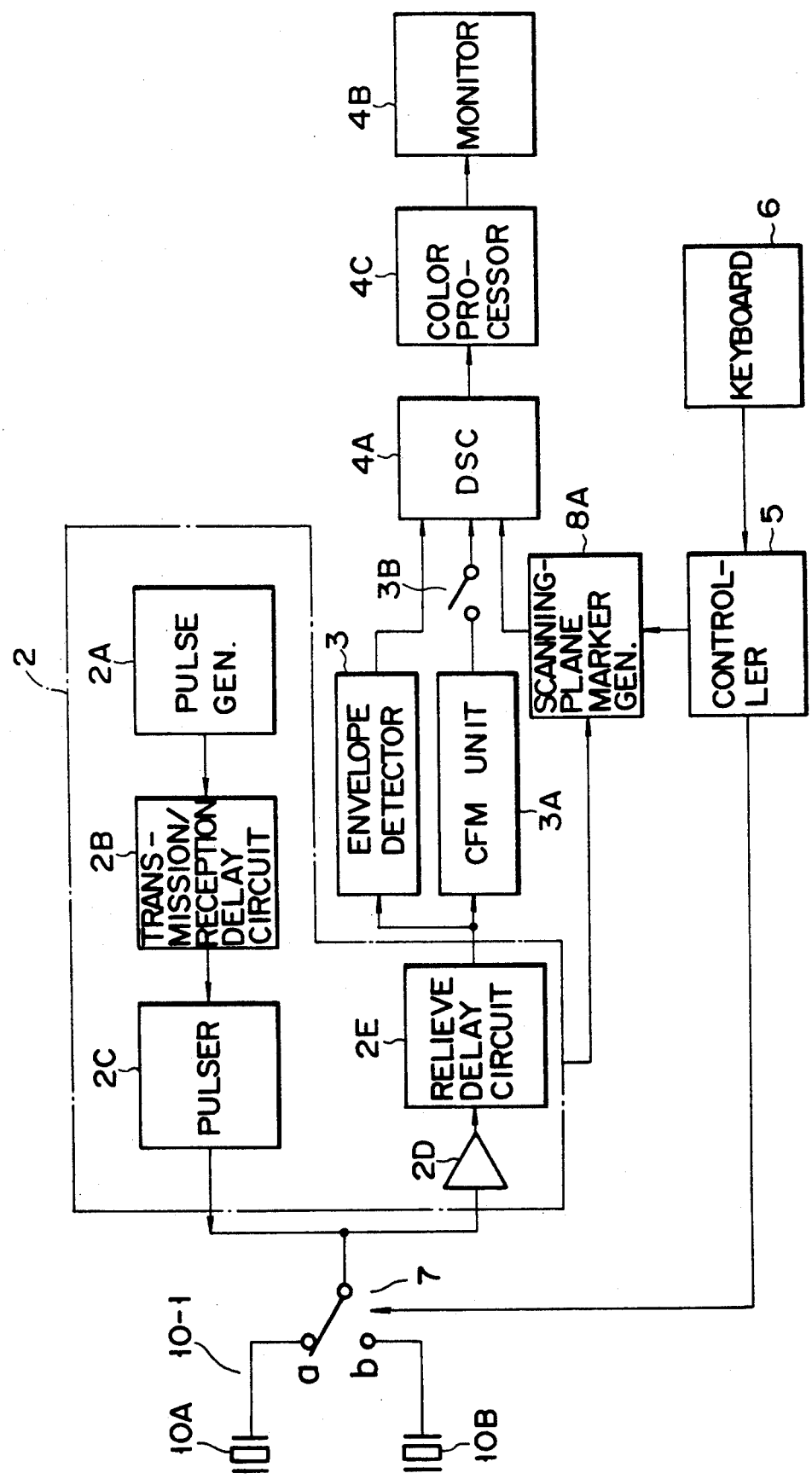
F I G. 14

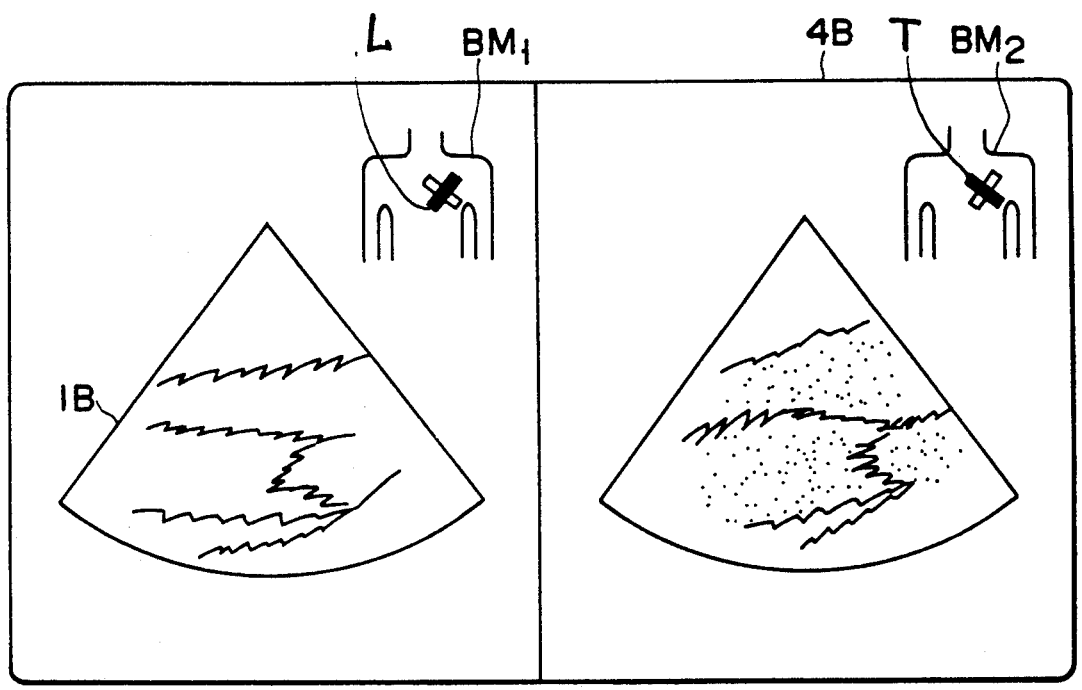
F I G. 19

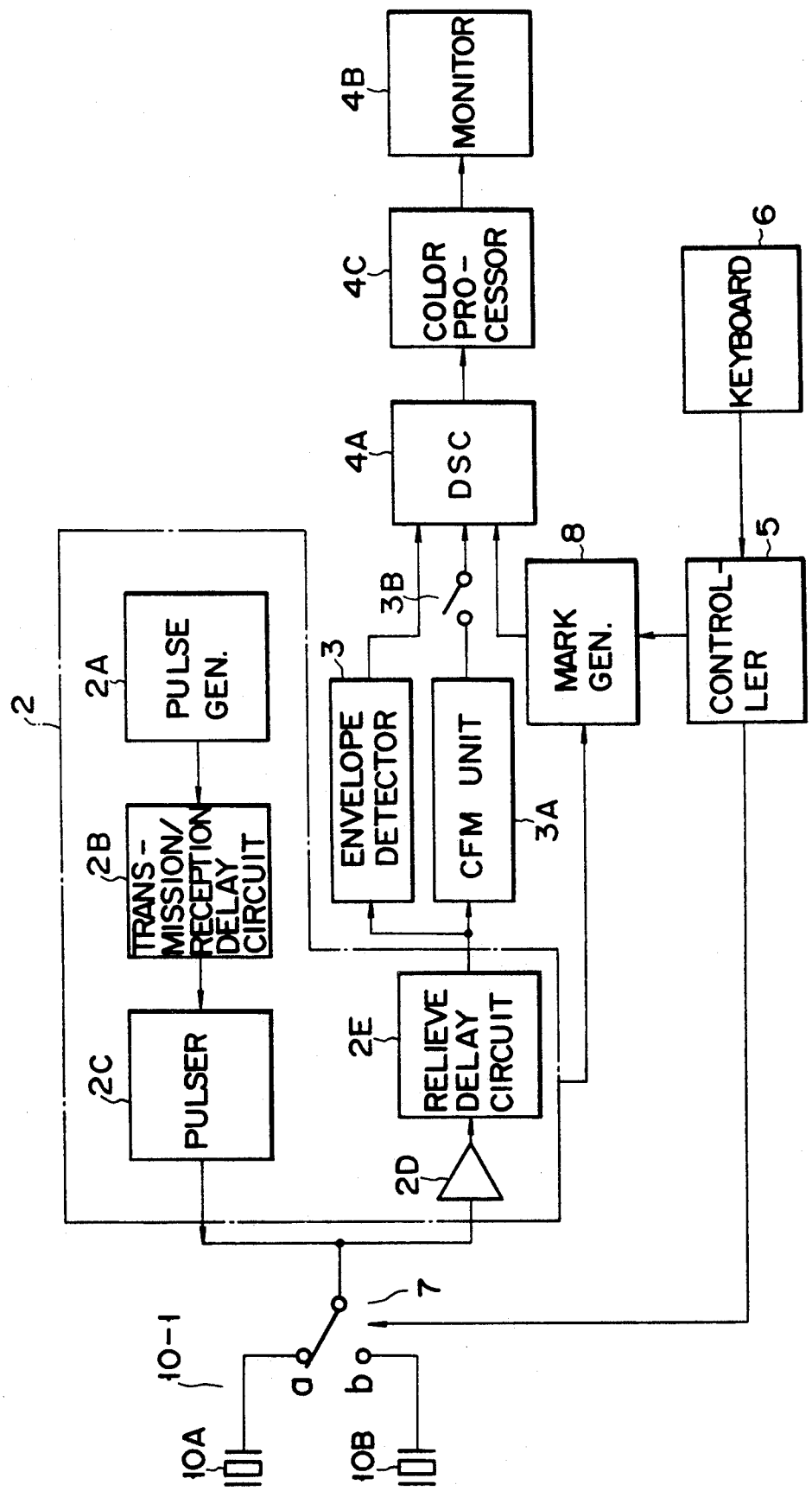
F I G. 20

ULTRASONIC DIAGNOSIS APPARATUS

BACKGROUND OF THE INVENTION

1. Field of the Invention

The present invention relates to an ultrasonic diagnosis apparatus which uses, for example, a biplane ultrasonic transducer to transmit and receive ultrasonic waves to and from a subject under examination and obtains ultrasonic cross-sectional images in two orthogonal scanning planes of the subject.

2. Description of the Related Art

The use of ultrasonic waves permits acquisition of cross-sectional images and blood flow information of a subject under examination. An ultrasonic imaging apparatus is constructed from an ultrasonic probe having an ultrasonic transducer, an ultrasonic-wave transmitting-receiving circuit system, a signal processing circuit, and a display unit. Upon receipt of an excitation pulse from the ultrasonic-wave transmitting-receiving circuit system, the ultrasonic transducer of the ultrasonic probe transmits ultrasonic waves. The reflected waves are received by the same transducer, so that a received signal is obtained. The received signal is processed by the signal processing circuit and then visually displayed by the display unit.

As such an apparatus there is what is referred to as an electronic scanning type apparatus. This type of apparatus uses an ultrasonic transducer comprised of a large number of electro-acoustic transducing elements, such as piezoelectric elements, which are arranged side by side. By driving each of the elements with a different amount of delay, ultrasonic waves are focused and deflected whereby an ultrasonic cross-sectional image can be obtained in real time.

Ultrasonic probes include probes for body cavity imaging and probes for body surface imaging, which are variously used, depending on the imaging desired. The body-cavity ultrasonic probe has an ultrasonic transducer to which a multiconductor cable is connected. The ultrasonic transducer is incorporated into one end of a bar. An operator holds the other end of the bar by hand and inserts the ultrasonic-wave transmitting-receiving plane of the ultrasonic transducer into such a body cavity as the anus of a subject under examination. The body-surface ultrasonic probe also has an ultrasonic transducer. The ultrasonic transducer is connected with a multiconductor cable and housed in a probe case. An operator holds the probe case by hand and puts the ultrasonic-wave transmitting-receiving plane of the ultrasonic transducer to the surface of a body region, such as the abdomen, of the subject.

The imaging of a body region is attained by obtaining a cross-sectional image in one scanning plane by the use of the body-cavity ultrasonic probe or the body-surface ultrasonic probe. An apparatus which is adapted to obtain cross-sectional images in two orthogonal planes and thus well suited for diagnosis has come into use recently.

Hereinafter a body-cavity ultrasonic probe and a body-surface ultrasonic probe which are adapted for imaging of two orthogonal planes will be described with reference to the drawings. Such a probe is also referred to as a biplane probe. That is, the body-cavity ultrasonic probe 1, as shown in FIG. 1, is designed so that an operator can hold the other end of a bar 22 by hand and insert the ultrasonic-wave transmitting-receiving plane of an ultrasonic transducer 1—1 into a body cavity. The ultrasonic transducer unit 1—1 comprises an ultrasonic transducer group 1A for obtaining a cross-sectional image in a lateral scanning plane A and an ultrasonic transducer group 1B for obtaining a cross-sectional image in a longitudinal plane B. In this case, the ultrasonic transducers groups 1A and 1B are made orthogonal to each other in the direction in which their elements are arranged, so that the scanning plane A and the scanning plane B are orthogonal to each other. In the present example, the ultrasonic transducer group 1A and the ultrasonic transducer group 1B are spaced as shown. The distance between the transducer group 1A and the transducer group 1B is d. In the case of sector scanning, the distance d stands for the distance between the ape of the sector scanning plane A and the apex of the sector scanning plane B, but not the distance 1 between the end of the transducer group 1A and the end of the transducer group 1B. In the present example, the distance d between the apex of the sector scanning plane A and the apex of the sector scanning plane B stands for the distance between the center of the elements of the transducer group 1A and the center of the elements of the transducer group 1B.

The body-surface ultrasonic probe 10, on the other hand, has an ultrasonic transducer unit 10-1 with substantially the same structure as the transducer unit shown in FIG. 1. The ultrasonic transducer unit 10-1 comprises ultrasonic transducer groups 10A and 10B. In the present example, the transducer group 10A and the transducer group 10B are disposed very close to each other. The distance between the transducer 10A and the transducer 10B is d'. In the case of sector scanning, the distance d, as in FIG. 1, stands for the distance between the apex of the sector scanning plane A and the apex of the sector scanning plane B, but not the distance 1 between the end of the transducer group 1A and the end of the transducer group 1B. In the present example, the distance 1 is substantially zero.

In the above examples, with the body-cavity ultrasonic probe 1, the transducer groups 1A and 1B are disposed with a space therebetween, while, with the body-surface ultrasonic probe 10, the transducer groups 10A and 10B are disposed very close to each other. Alternatively, the transducer groups 10A and 10B may be disposed very close to each other in the body-surface ultrasonic probe 10, while the transducer groups 1A and 1B may be disposed with a space therebetween in the body-cavity ultrasonic probe 1.

As shown in FIG. 2, the ultrasonic transducer unit 10-1 is incorporated in an end of a probe case 10-2. A cable 10-3 emerges from the other end of the probe case 10-2. FIG. 3A and FIG. 3B are a front view and a side view of the body-surface ultrasonic probe 10 and FIG. 3b, respectively. As can be seen from FIGS. 3A and 3B, cross-sectional images in the orthogonal scanning planes A and B can be obtained by putting the ultrasonic transducer 10-1 of the body-surface ultrasonic probe 10 to the body surface.

As described above, the transducer groups 1A and 1B in the body-surface ultrasonic probe 1 are disposed with a distance d therebetween, while the transducer groups 10A and 10B in the body-surface ultrasonic probe 10 are disposed with a distance d' therebetween. For this reason, in order to obtain a cross-sectional image in the scanning plane B after a cross-sectional image in the scanning plane A has been obtained, the probe must be moved to a position in the scanning plane B. This will impose a burden on an operator and the examination will be prolonged.

With either of the body-cavity ultrasonic probe 1 and the body-surface ultrasonic probe 10, switching between the ultrasonic transducers is required in order to display a cross-sectional image in a scanning plane after the display of a cross-sectional image in the other scanning plane. The probe must then be moved to a desired position for display of the cross-sectional image in the former scanning plane. It is therefore difficult for an operator to understand the scanning plane of a cross-sectional image which is being displayed on the display screen. Thus, it becomes difficult to make diagnosis efficiently and moreover the examination takes a long time.

SUMMARY OF THE INVENTION

It is accordingly a first object of the present invention to provide an ultrasonic diagnosis apparatus which permits imaging of multiple scanning planes without the need of operating a probe many times so that the burden of an operator can be alleviated and moreover the examination time can be shortened.

It is a second object of the present invention to provide an ultrasonic diagnosis apparatus which permits an operator to easily understand the correspondence between a cross-sectional image which is being displayed, which is one of cross-sectional images in plural scanning planes, and its scanning plane, thereby improving the efficiency of diagnosis.

According to an aspect of the present invention there is provided an ultrasonic diagnosis apparatus comprising:

an ultrasonic probe having a plurality of ultrasonic transducers to form ultrasonic scanning planes;

selecting means for selecting at least one of said ultrasonic transducers;

driving means for driving at least one of said ultrasonic transducers selected by said selecting means to transmit and receive ultrasonic waves;

ultrasonic-image producing means responsive to a received signal from an ultrasonic transducer driven by said driving means to produce an ultrasonic image;

scanning-plane mark generating means for generating a scanning-plane mark adapted to indicate the positional relationship between the ultrasonic scanning plane formed by an ultrasonic transducer selected by said selecting means and the ultrasonic scanning plane formed by the other ultrasonic transducer; and display means for displaying an ultrasonic image produced by said ultrasonic image producing means and said scanning-plane mark generated by said scanning-plane mark generating means.

According to another aspect of the present invention there is provided an ultrasonic diagnosis apparatus comprising:

an ultrasonic probe having a plurality of ultrasonic transducers to form ultrasonic scanning planes;

selecting means for selecting at least one of said ultrasonic transducers;

driving means for driving at least one of said ultrasonic transducers selected by said selecting means to transmit and receive ultrasonic waves;

ultrasonic-image producing means responsive to a received signal from an ultrasonic transducer driven by said driving means to produce an ultrasonic image;

probe mark generating means for generating a probe mark adapted to indicate the positional relationship between the ultrasonic scanning plane formed by an ultrasonic transducer selected by said selecting means and the ultrasonic scanning plane formed by the other ultrasonic transducer by use of an illustration of said ultrasonic probe; and display means for displaying an ultrasonic image produced by said ultrasonic image producing means and said probe mark generated by said probe mark generating means.

According to still another aspect of the present invention there is provided an ultrasonic diagnosis apparatus comprising:

an ultrasonic probe having a plurality of ultrasonic transducers to form ultrasonic scanning planes;

selecting means for selecting at least one of said ultrasonic transducers;

driving means for driving at least one of said ultrasonic transducers selected by said selecting means to transmit and receive ultrasonic waves;

ultrasonic-image producing means responsive to a received signal from an ultrasonic transducer driven by said driving means to produce an ultrasonic image;

body mark generating means for generating a body mark adapted to indicate the relationship in position on a subject under examination between the ultrasonic scanning plane formed by an ultrasonic transducer selected by said selecting means and the ultrasonic scanning plane formed by the other ultrasonic transducer by use of an illustration of a subject under examination and/or said ultrasonic probe; and display means for displaying an ultrasonic image produced by said ultrasonic image producing means and said body mark generated by said body mark generating means.

According to a further aspect of the present invention there is provided an ultrasonic diagnosis apparatus comprising:

an ultrasonic probe having a plurality of ultrasonic transducers to form ultrasonic scanning planes;

selecting means for selecting at least one of said ultrasonic transducers;

driving means for driving at least one of said ultrasonic transducers selected by said selecting means to transmit and receive ultrasonic waves;

ultrasonic-image producing means responsive to a received signal from an ultrasonic transducer driven by said driving means to produce an ultrasonic image;

mark generating means for generating a scanning-plane mark adapted to indicate the relationship in position on a subject under examination between the ultrasonic scanning plane formed by an ultrasonic transducer selected by said selecting means and the ultrasonic scanning plane formed by the other ultrasonic transducer and/or a probe mark adapted to indicate the relationship in position on a subject under examination between the ultrasonic scanning plane formed by an ultrasonic transducer selected by said selecting means and the ultrasonic scanning plane formed by the other ultrasonic transducer by use of an illustration of said ultrasonic probe and/or a body mark adapted to indicate the relationship in position on a subject under examination between the ultrasonic scanning plane formed by an ultrasonic transducer selected by said selecting means and the ultrasonic scanning plane formed by the other ultrasonic transducer by use of an illustration of said subject under examination and/or said ultrasonic probe; and display means for displaying an ultrasonic image produced by said ultrasonic image producing means and said marks generated by said mark generating means.

According to an aspect of the present invention there is provided an ultrasonic diagnosis apparatus comprising:

an ultrasonic probe having a plurality of ultrasonic transducers to form ultrasonic scanning planes;

selecting means for selecting at least one of said ultrasonic transducers;

driving means for driving at least one of said ultrasonic transducers selected by said selecting means to transmit and receive ultrasonic waves;

ultrasonic-image producing means responsive to a received signal from an ultrasonic transducer driven by said driving means to produced an ultrasonic image;

character information generating means for generating a character information adapted to indicate the positional relationship between the ultrasonic scanning plane formed by an ultrasonic transducer selected by said selecting means and the ultrasonic scanning plane formed by the other ultrasonic transducer; and display means for displaying an ultrasonic image produced by said ultrasonic image producing means and said character information generated by said character information generating means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 7A and 7B illustrate cross-sectional images IB obtained by the ultrasonic transducer group 1B in FIG. 4;

FIG. 7C illustrates a cross-sectional image obtained by the ultrasonic transducer group 1A in FIG. 4;

FIG. 8 illustrates a simultaneous display format of a cross-sectional image IB produced by the ultrasonic transducer group 1B, a cross-sectional image IA produced by the ultrasonic transducer group 1A and scanning-plane marks indicating the scanning planes of the cross-sectional images;

FIG. 12 is a block diagram of an ultrasonic diagnosis apparatus according to a third embodiment of the present invention;

FIG. 13 illustrates a simultaneous display format of a cross-sectional image IB produced by the ultrasonic transducer group 1B, a cross-sectional image IA produced by the ultrasonic transducer group 1A of the apparatus of FIG. 12, scanning-plane marks and probe marks;

FIG. 14 is a bock diagram of an ultrasonic diagnosis apparatus according to a fourth embodiment of the present invention;

FIG. 19 illustrates a simultaneous display format of a cross-sectional image IB produced by the ultrasonic transducer group 10B, a BDF image produced by the ultrasonic transducer group 10A of the apparatus of FIG. 18 and body marks;

FIG. 20 is a block diagram of an ultrasonic diagnosis apparatus according to a seventh embodiment of the present invention;

DETAILED DESCRIPTION OF THE PREFERRED EMBODIMENTS

Hereinafter a description will be made of an electronic sector scanning type ultrasonic diagnosis apparatus as a first embodiment of the present invention.

Figure 4:
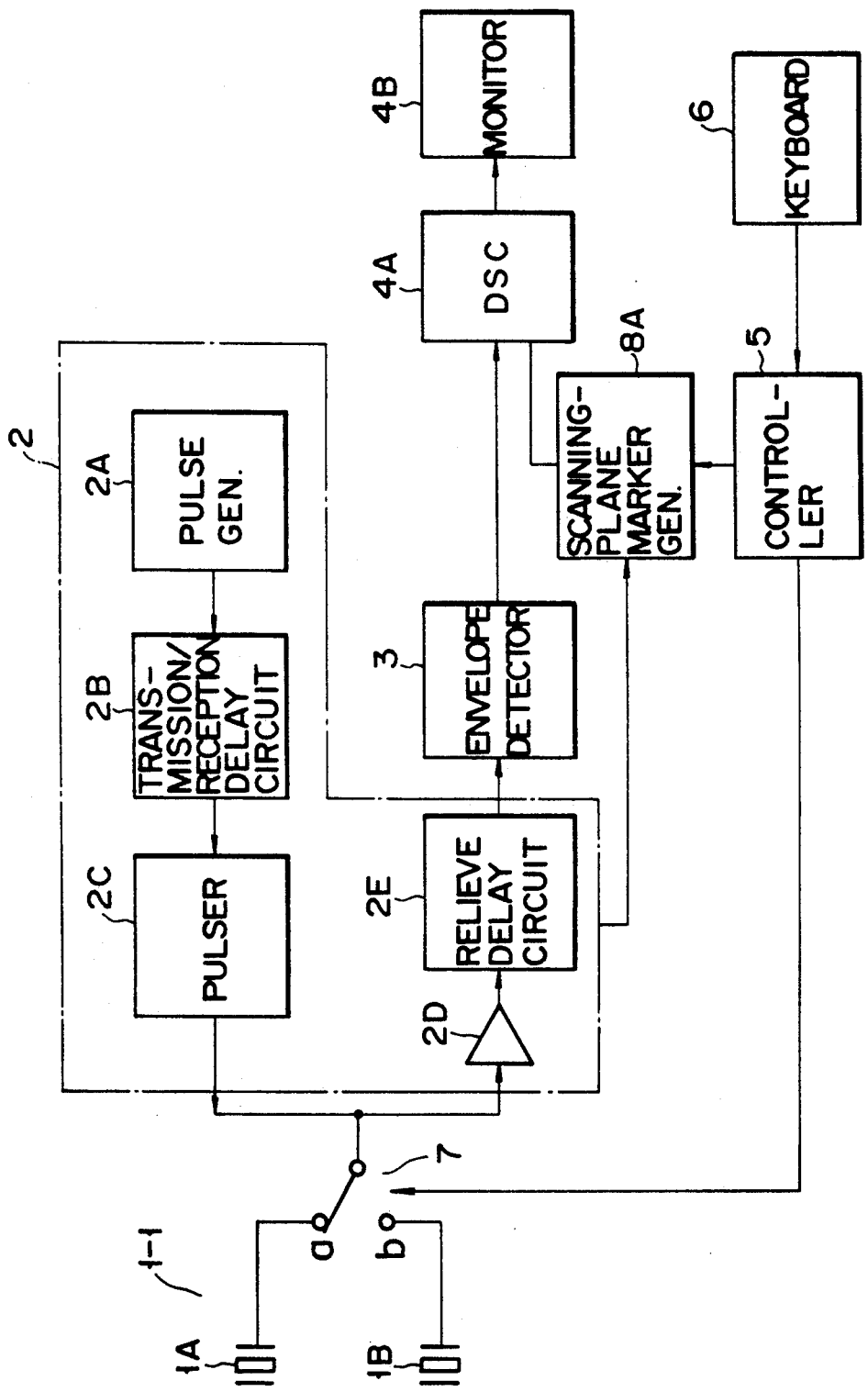
FIG. 4 is a block diagram of an ultrasonic diagnosis apparatus according to a first embodiment of the present invention.

Referring now to FIG. 4, the ultrasonic diagnosis apparatus according to the first embodiment is constructed from an ultrasonic transducer unit 1—1 which is the main component of a body-cavity ultrasonic probe 1, a transmitting-receiving system 2 (2A, 2B, 2C, 2D, 2E), a B-mode processing system 3, a video system 4 (4A, 4B) and a control system (5, 6, 7, 8).

Figure 5:
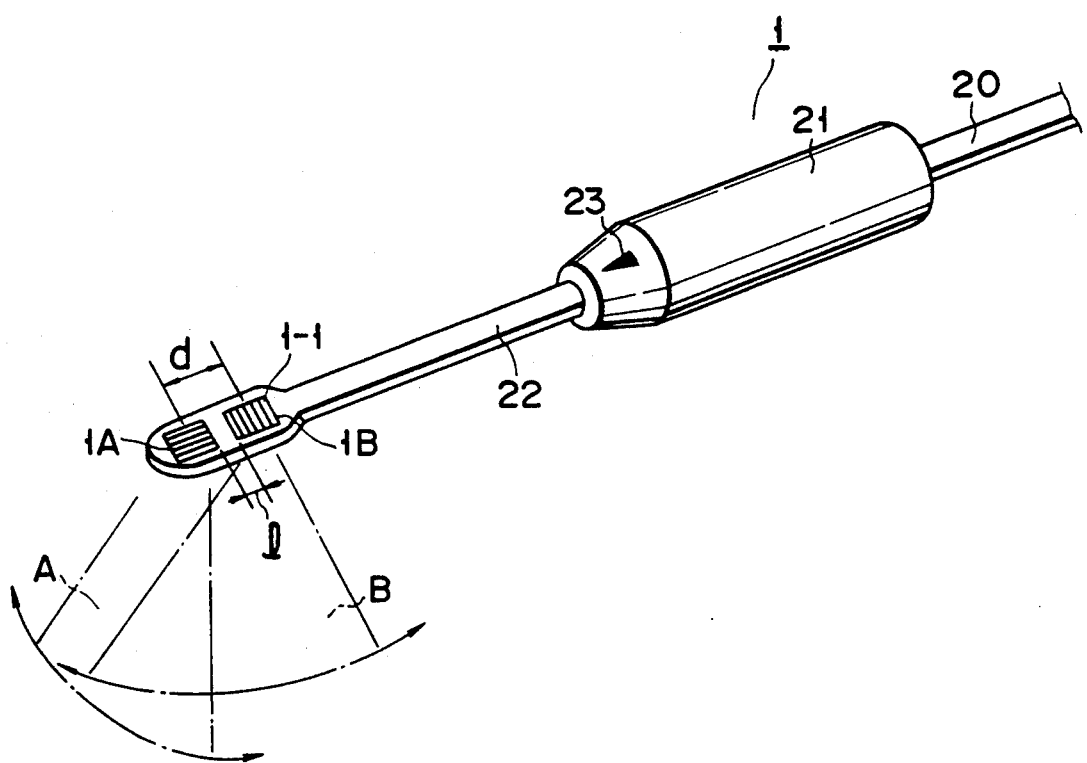
FIG. 5 is a perspective view of a body-cavity ultrasonic probe having two ultrasonic transducer groups.
Figure 6:
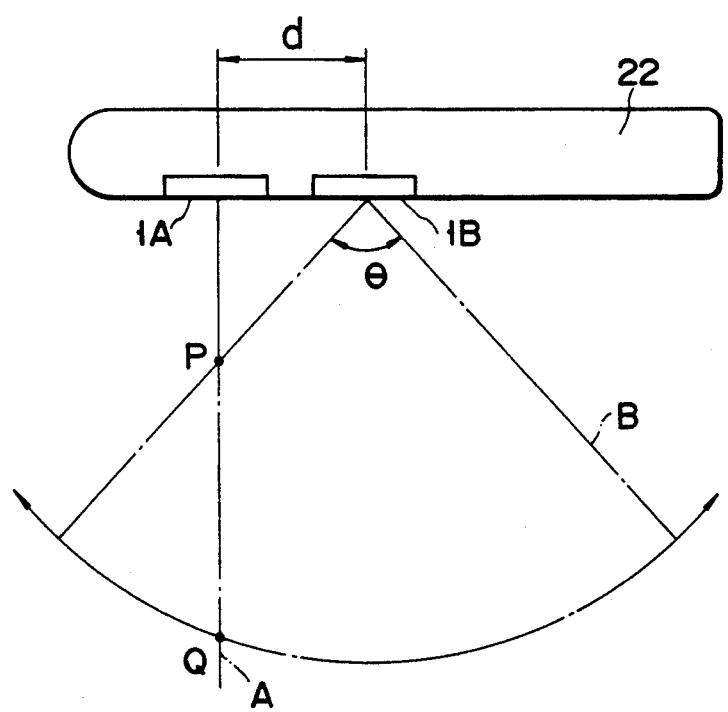
FIG. 6 illustrates the center-to-center distance d of two orthogonal ultrasonic transducer groups and the positional relationship between a scanning plane A and a scanning plane B.

The body-cavity ultrasonic probe 1 is constructed, as shown in FIG. 5, from a cable 20, a grip 21 and a bar 22. That is, the cable 20, which is used for supplying signals to the ultrasonic transducer unit 1—1 and transmitting received signals from the ultrasonic transducer unit 1—1 to the outside, is connected to emerge from an end of the grip 21. Into the other end of the grip is inserted the bar 22. The ultrasonic transducer unit 1—1 is provided on the tip of the bar 22. A mark, formed on the grip 21 and indicated at 22, is adapted to designate the direction of scanning of a reference cross-sectional image for an operator.

The ultrasonic transducer unit 1—1, as shown in FIG. 5, has two ultrasonic transducer groups 1A and 1B. In this embodiment, the distance between the transducer groups 1A and group 1B is d. In the case of sector scanning, the distance d stands for the distance between the apex of the sector scanning plane A and the apex of the sector scanning plane B but not the distance between the end of the transducer group 1A and the end of the transducer group 1B. In this embodiment, the distance d between the apex of the sector scanning plane A and the apex of the sector scanning plane B corresponds to the center-to-center distance of the transducer groups 1A and 1B. Each of the ultrasonic transducer groups 1A and 1B can transmit and receive pulses of ultrasonic waves. Each of the ultrasonic transducer groups 1A and 1B comprises a large number of piezoelectric ceramic elements which are arranged side by side. The ultrasonic transducer group 1A can obtain a cross-sectional image (i.e., a B-mode image) in the scanning plane A indicated by dash-dotted lines, while the ultrasonic transducer group 1B can obtain a cross-sectional image in the scanning plane B indicated by dash-dotted lines. The ultrasonic transducer groups 1A and 1B are orthogonal to each other with respect to their direction of arrangement of the piezoelectric elements. Thus, the cross-sectional image in the scanning plane A and the cross-sectional image in the scanning plane B are orthogonal to each other, so that cross-sectional images in the two orthogonal scanning planes can be obtained. Although, in this embodiment, the ultrasonic transducer groups 1A and 1B are orthogonal to each other in their direction of arrangement of piezoelectric elements, they, of course, need not be orthogonal to each other.

Returning to FIG. 4, the transmitting-receiving system 2 is comprised of a pulse generator 2A, a transmission delay circuit 2B, a pulser 2C, a preamplifier 2D and a reception delay circuit 2E. The pulse generator 2A supplies rate pulses to the transmission delay circuit 2B. The transmission delay circuit 2B introduces time delays to the rate pulses. The delayed rate pulses are applied to the pulser 2C. The pulser 2C is responsive to the delayed rate pulses to drive the ultrasonic transducer group 1A and/or the ultrasonic transducer group 1B for electronic sector scan. When driven by the pulser 2C, the ultrasonic transducer groups 1A and 1B transmit pulses of ultrasonic waves to a living organism not shown. Ultrasonic waves reflected from the inside of the living organism are received by the ultrasonic transducer groups 1A and 1B. When received signals are applied from the transducers to the transmitting-receiving system 2, the preamplifier 2D amplifies the received signals and applies them to the reception delay circuit 2E. The receive delay circuit 2E introduces a time delay to a received signal from each of the transducer elements so as to cancel out the time delay which was introduced to the transmit signal to the corresponding transducer element at the time of transmission.

The B-mode processing system comprises an envelope detector 4 which detects the envelope of a received signal output from the receive delay circuit 2E through a logarithmic amplifier (not shown) to yield ultrasonic imaging data. The ultrasonic imaging data is written into the DSC (digital scan converter) 4A.

The video system comprises a DSC 4A and a TV monitor 4B. The DSC 4A is provided with a large-capacity memory having a first memory area for storing data on a cross-sectional image in the scanning plane A and a second memory area for storing data on a cross-sectional image in the scanning plane B. The DSC 4A stores a mark display signal generated from a mark generator 8 for each of the scanning planes A and B in a respective portion of its first and second memory areas. The DSC 4A is further provided with at least two frame memories for storing image data in the scanning planes A and B, respectively, on a frame-by-frame basis. The image data stored in each frame memory is subjected to ultrasonic scan-to-TV scan conversion and then applied to the TV monitor 4B. The TV monitor 4B displays the cross-sectional images in the scanning planes A and B corresponding to the ultrasonic transducers 1A and 1B individually, alternately or simultaneously.

The control system is comprised of a controller 5, a keyboard 6, a switch 7 and a scanning-plane indicating mark generator 8A. The controller 5 is responsive to an operator command from the keyboard 6 to apply to the switch 7 a switching control signal for switching between the ultrasonic transducer groups 1A and 1B. Also, the controller 5 issues a command to the scanning-plane mark generator 8A. The scanning-plane mark generator 8A employs at least information about the ultrasonic transducer groups 1A and 1B, information about the distance d between the transducer groups 1A and 1B and information about a sector scanning angle 8 so as to display scanning-plane marks SM, indicating the positional relationship between the scanning planes A and B, on ultrasonic images displayed on the TV monitor 4B. Of the scanning-plane marks, a mark SM1 indicates the position of the scanning plane A in the scanning plane B, while a mark SM2 indicates the position of the scanning plane B in the scanning plane A. The scanning-plane mark SM1 appears at the left or right end of the scanning plane B, while the scanning-plane mark SM2 appears at the center of the scanning plane A. Each of the marks SM is expressed by a line or a series of dots. The scanning-plane marks SM, unlike a probe mark and a body mark which will be described later, are displayed superimposed on corresponding sector images (cross-sectional images). Each of the probe mark and the body mark is not superimposed on a sector image.

Next, the operation of the first embodiment of the present invention will be described with reference to FIGS. 7A, 7B and 7C. First, an operator holds the grip 21 of the ultrasonic probe 1 and inserts the ultrasonic transducer unit 1—1 into a body cavity of a living body in order to obtain a cross-sectional image IB containing a region of interest ROI. The operator then operates the keyboard 6 so that the controller 5 will places the switch 7 in the position b. Ultrasonic waves are consequently transmitted from the ultrasonic transducer group 1B into the body cavity. Subsequently, received signals are detected by the envelope detector 3A and image data in the scanning plane B is written into the DSC 4A.

On the other hand, upon receipt from the controller 5 of information indicating that, of the ultrasonic transducer groups 1A and 1B, it is the ultrasonic transducer group 1B that is performing ultrasonic imaging, the mark generator 8 generates a mark display signal for displaying the scanning-plane mark SM1 indicating the positional relationship between the scanning planes A and B on the basis of the information on the ultrasonic transducer groups 1A and 1B, the information on the distance d between the transducer groups 1A and 1B and the sector scanning angle $\theta$. The mark display signal is then applied to the DSC 4A. The cross-sectional image IB and the scanning-plane mark SM1 are thus displayed on the screen of the TV monitor 4B as shown in FIG. 7A.

Next, after the display of the cross-sectional image IB the cross-sectional image IA in the scanning plane A can be obtained in the following manner. First, as shown in FIG. 7B, the ultrasonic probe 1 is moved to the right so that the region of interest ROI will position on the scanning-plane mark SM1. When the switch 7 is then set to the position a by the controller 5, ultrasonic waves are transmitted from the ultrasonic transducer group 1A into the body cavity, so that received signals are detected by the envelope detector 3A and cross-sectional image data in the scanning plane B is written into the DSC 4A. Thus, as shown in FIG. 7C, a cross-sectional image in the scanning plane A can be displayed on the TV monitor 4B, with the region of interest ROI positioned on the center of the image. Therefore, the cross-sectional image IA in the scanning plane A and the cross-sectional image IB in the scanning plane B can be displayed simultaneously on the TV monitor 4B as shown in FIG. 8.

In such a case, since only one of the transducer groups 1A and 1B can be driven, the cross-sectional image IA obtained by the transducer group 1A is displayed in real time, but the image IB obtained by the transducer group 1B is not displayed in real time. For example, the image IB in the scanning plane B is displayed in the form of a still image. The still-image display can be realized by reading the cross-sectional image IB from the frame memory in the DSC 4A over and over again and applying it to the TV monitor 4B. Of course, only one of the ultrasonic cross-sectional images IA and IB may be displayed. Furthermore, the images IA and IB may be displayed alternately.

As described above, the cross-sectional image IB in the scanning plane B is displayed first. At this point the scanning-plane mark SM1 on the image IB indicates the position of the scanning plane A. By simply moving the body-cavity ultrasonic probe 1 only once so that the region of interest ROI may position on the scanning-plane mark SM1, the cross-sectional image IA having the ROI set at its center can be obtained. Thereby, the cross-sectional images IA and IB in the orthogonal scanning planes A and B can be displayed simultaneously on the TV monitor 4B as shown in FIG. 8. Thus, good ultrasonic diagnosis information is obtainable. Further, the burden on the operator can be decreased and the examination time can be shortened. Of course, the images IA and IB can be displayed individually or simultaneously.

The above embodiment may be modified in various ways. The ultrasonic transducer groups 1A and 1B may be provided on opposite surfaces of the bar 22 at its one end with their transducer elements arranged in different directions.

Figure 9:
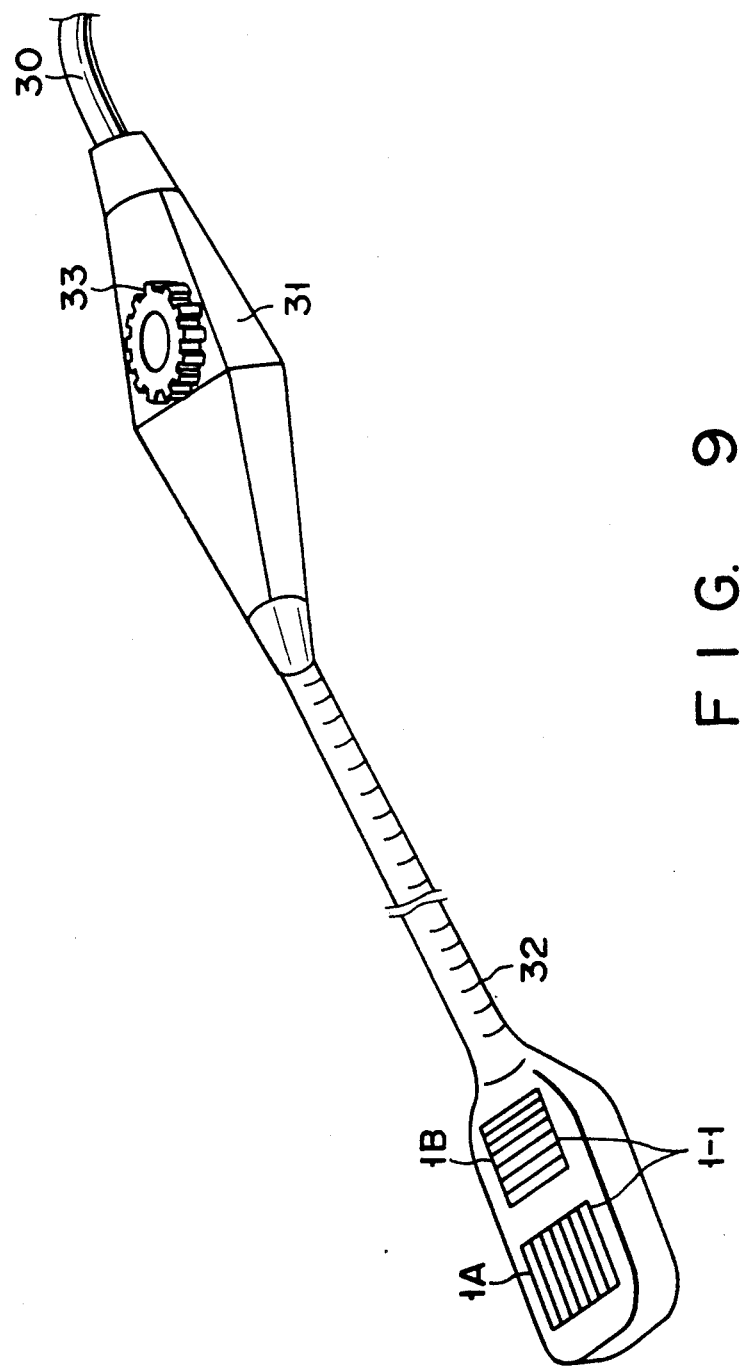
FIG. 9 is a perspective view of a probe used for examining the esophagus.

Furthermore, the present invention, as shown in FIG. 9, may be adapted to an esophagus ultrasonic probe to be inserted into the esophagus for ultrasonic imaging of the heart therefrom.

The esophagus ultrasonic probe is constructed as follows. A cable 30 is connected to emerge from a grip 31. The grip is provided with a flexible bar 32. The flexible bar is equipped with the ultrasonic transducer unit 1—1 at its tip. The grip is further provided with an angle knob 33 for driving an angle mechanism. If, therefore, an operator holds the grip 31 and operates the angle knob 33, then the flexible bar 32 can be bent in any direction. For this reason, the ultrasonic transducer unit 1—1 can be placed in any position. Although, in the above embodiment, the ultrasonic transducer groups 1A and 1B were described as being adapted for electronic sector scanning, they may be adapted for some other electronic scanning such as electronic linear scanning or electronic convex scanning.

Figure 1:
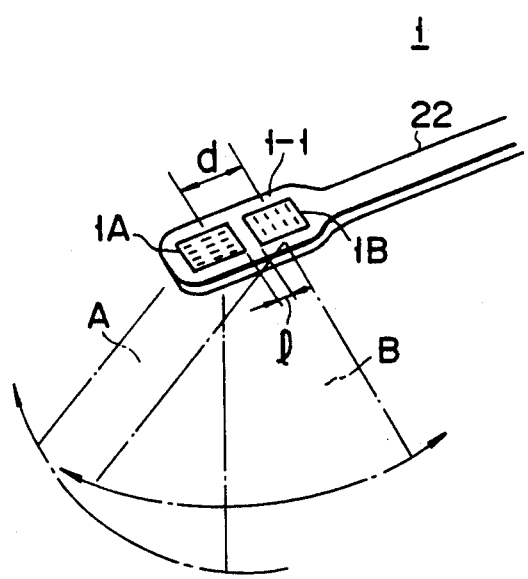
FIG. 1 is a diagrammatic view of a body-cavity ultrasonic probe having two ultrasonic transducers and ultrasonic scanning of a longitudinal scanning plane and a lateral scanning plane.
Figure 2:
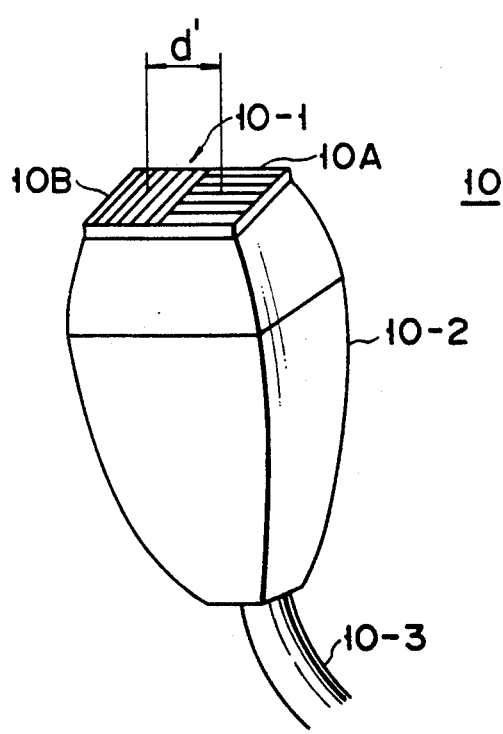
FIG. 2 is a perspective view of a body-surface ultrasonic probe having two ultrasonic transducer groups.
Figure 3A:
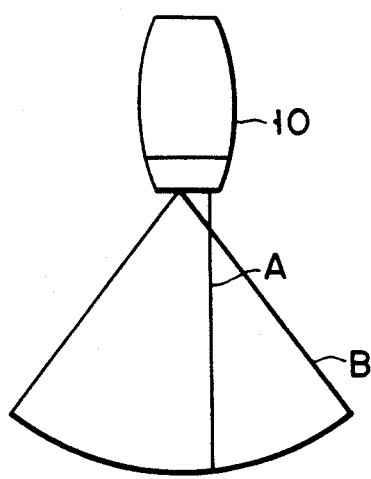
FIGS. 3A and 3B illustrate longitudinal and lateral scanning planes scanned by means of the body-surface ultrasonic probe shown in FIG. 2.
Figure 3B:
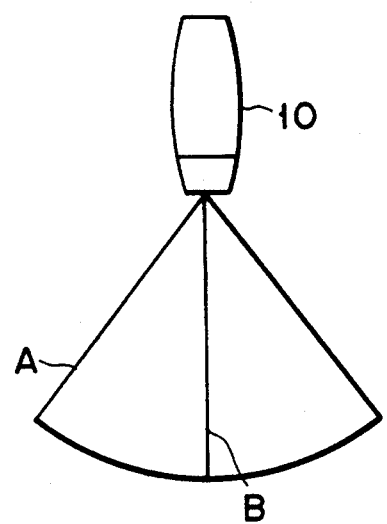

Although the above embodiment is applied to the body-cavity ultrasonic probe 1 shown in FIG. 5 or 1, it may be applied to the body-surface ultrasonic probe 10 shown in FIG. 2 in place of the body-cavity ultrasonic probe.

Figure 10:
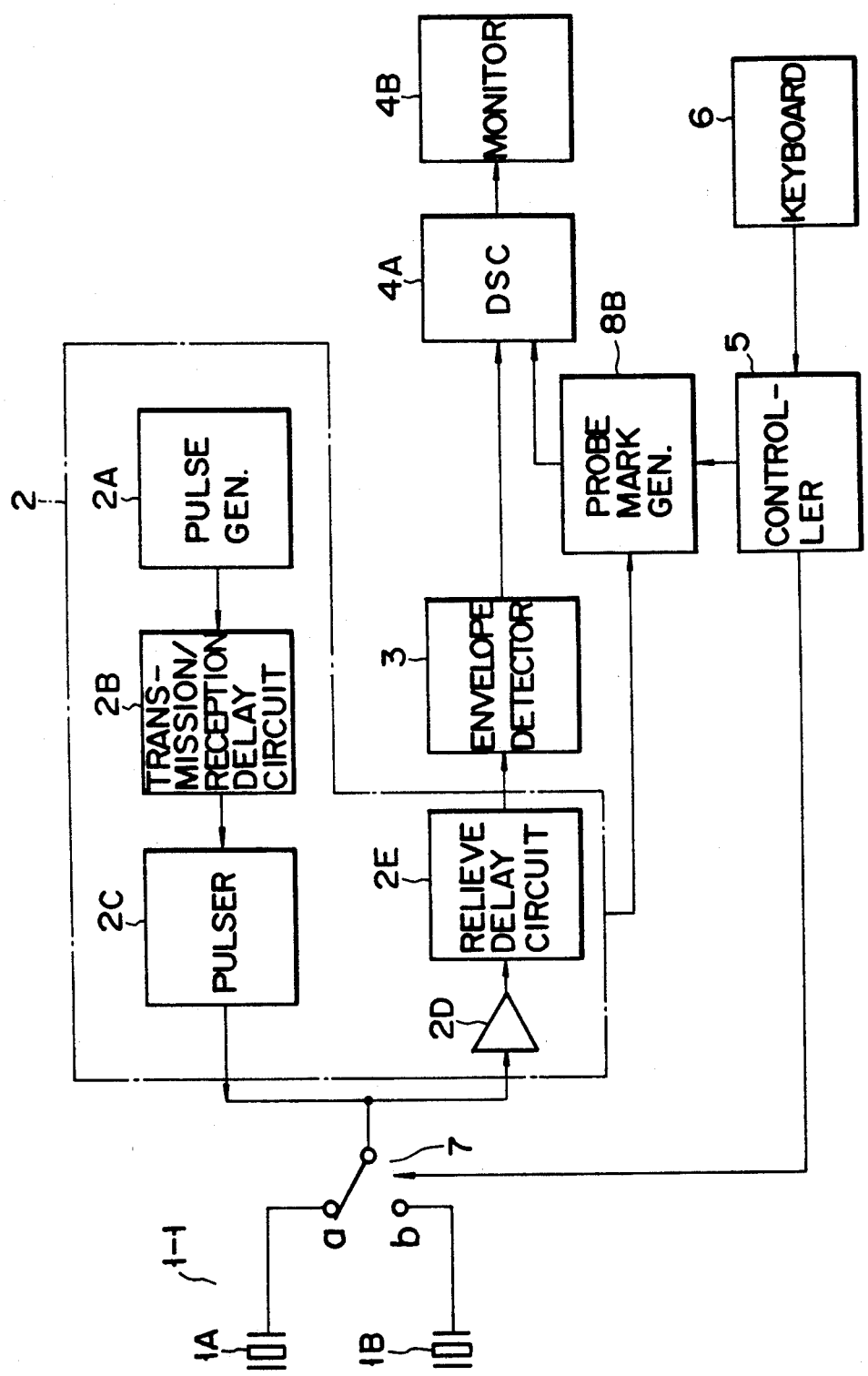
FIG. 10 is a block diagram of an ultrasonic diagnosis apparatus according to a second embodiment of the present invention.
Figure 11:
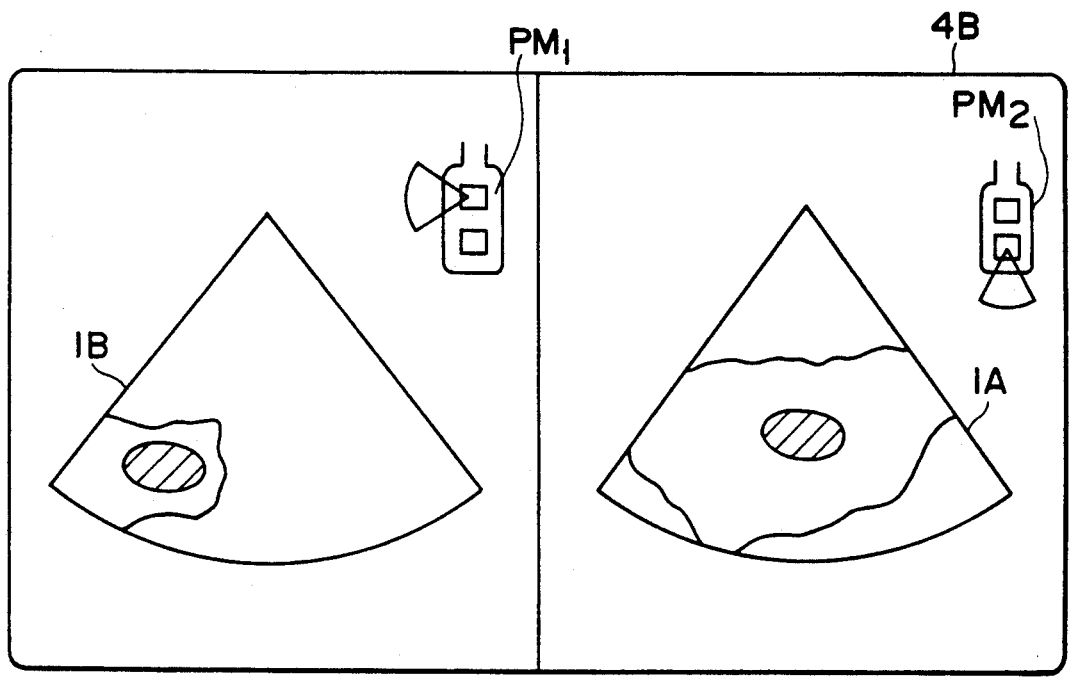
FIG. 11 illustrates a simultaneous display format of a cross-sectional image IB produced by the ultrasonic transducer group 1B, a cross-sectional image IA produced by the ultrasonic transducer group 1A of the apparatus of FIG. 10 and probe marks.

A second embodiment of the present invention will be described next with reference to FIGS. 10 and 11. The second embodiment, as shown in FIG. 10, is provided with a probe mark generator 8B in place of the scanning-plane mark generator 8A. When information about the transducer groups 1A and 1B is supplied from the controller 5 to the probe mark generator 8B, probe marks PM1 and PM2 are displayed near the ultrasonic cross-sectional image IB in the scanning plane B and the ultrasonic cross-sectional image IA in the scanning plane A, respectively. The probe mark PM1 indicates that the image IB is obtained by the transducer group 1B, while the probe mark PM2 indicates that the image 1A is obtained by the transducer group 1A. In other words, the probe marks PM indicate the positional relationship between the scanning plane A formed by the transducer group 1A for the image IB and the scanning plane B formed by the transducer group 1B for the image IB by the use of illustrations of the probe 1. Where the images IA and IB are displayed simultaneously, one of them is a real-time image and the other is a frozen image. Where the images IA and IB are displayed alternately, the image IA is displayed in real time and the image IB is not displayed or displayed in a freeze mode. After the real-time display of the image IA the image IB is displayed in real time.

A third embodiment of the present invention will be described below with reference to FIGS. 12 and 13. This embodiment, as shown in FIG. 12, is provided with a scanning-plane-mark and probe-mark generator 8C in place of the scanning-mark generator 8A or the probe-mark generator 8B. As a result, when information about the ultrasonic transducer groups 1A and 1B is applied from the controller 5 to the mark generator 8C, the scanning-plane mark SM1 is displayed superimposed on the cross-sectional image IB in the scanning plane B and moreover the probe mark PM1 is displayed in the neighborhood of the cross-sectional image IB. At the same time, the scanning-plane mark SM2 is displayed superimposed on the cross-sectional image IA in the scanning plane A, and moreover the probe mark PM2 is displayed in the neighborhood of the image IB.

Figure 15:
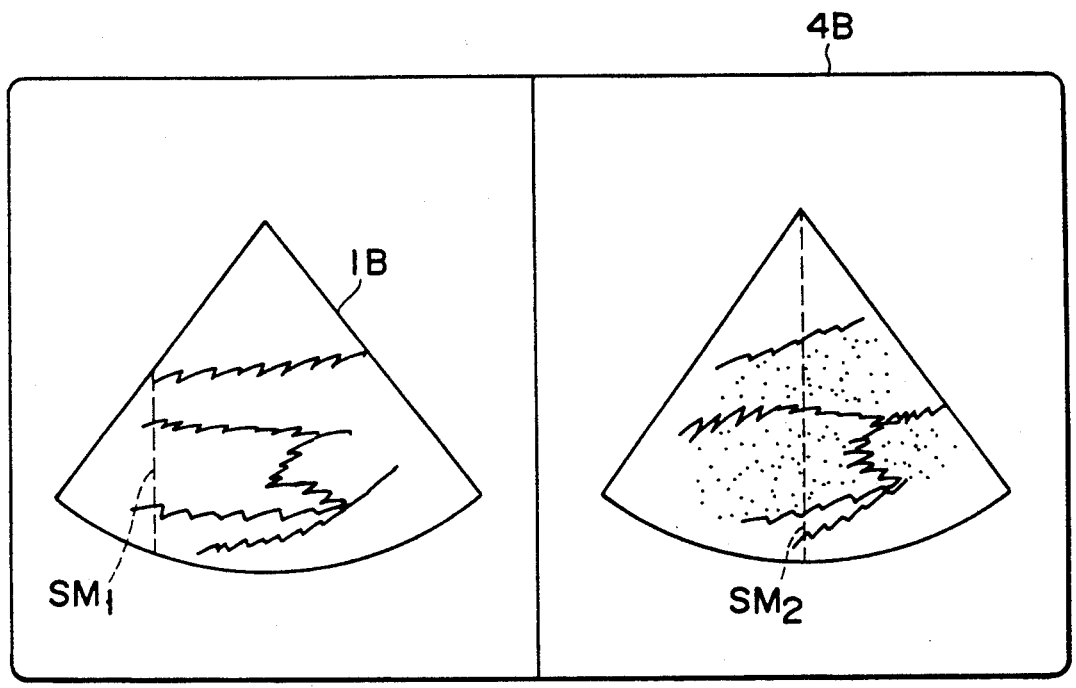
FIG. 15 illustrates a simultaneous display format of a cross-sectional image IB produced by the ultrasonic transducer group 10B, a BDF image produced by the ultrasonic transducer group 10A of the apparatus of FIG. 14 and scanning-plane marks.

Next, a fourth embodiment of the present invention will be described with reference to FIGS. 14 and 15. This embodiment, as shown in FIG. 14, uses the body-surface ultrasonic probe 10 in place of the body-cavity ultrasonic probe in FIG. 4. Further, this embodiment is provided with a color flow mapping (CFM) unit 3A for blood flow imaging at the output side of the receive delay circuit 2E. CFM data from the CFM unit is applied to the DSC 4A via a switch 3B. Furthermore, a color processing circuit 4C is connected to the output of the DSC 4A so that a color-processed CFM image can be applied to the monitor 4B. This embodiment is the same as the embodiment shown in FIG. 4 in the other points. According to such an arrangement, a cross-sectional image can be obtained by the ultrasonic transducer unit 10-1 when the switch 3B is turned OFF, while a BDF image in which a CFM image is superimposed on the cross-sectional image can be obtained when the switch is turned ON. Thus, supposing that, for example, the switch 3B is OFF when the transducer 10B of the transducer unit 10-1 is selected and the switch 3B is ON when the transducer group 10A is selected, such a display image as shown in FIG. 15 will be obtained. As shown in FIG. 15, the cross-sectional image IB in the scanning plane B is obtained by the ultrasonic transducer 10B. At this point the scanning-plane mark SM1 is displayed superimposed on the image IB. Also, a BDF image in the scanning plane A is obtained by the transducer group 10A. The scanning-plane mark SM2 is displayed superimposed on the BDF image. In contrast with this, the switch 3B may be ON when the transducer 10B is selected in the transducer unit 10-1, while it may be OFF when the transducer group 10A is selected. In this case, a BDF image in the scanning plane B will be obtained by the transducer group 10B. The scanning-plane mark SM1 is displayed on the BDF image. Also, the cross-sectional image IA in the scanning plane A will be obtained by the transducer group 10A. The scanning-plane mark SM2 is displayed superimposed on the image IA.

Figure 16:
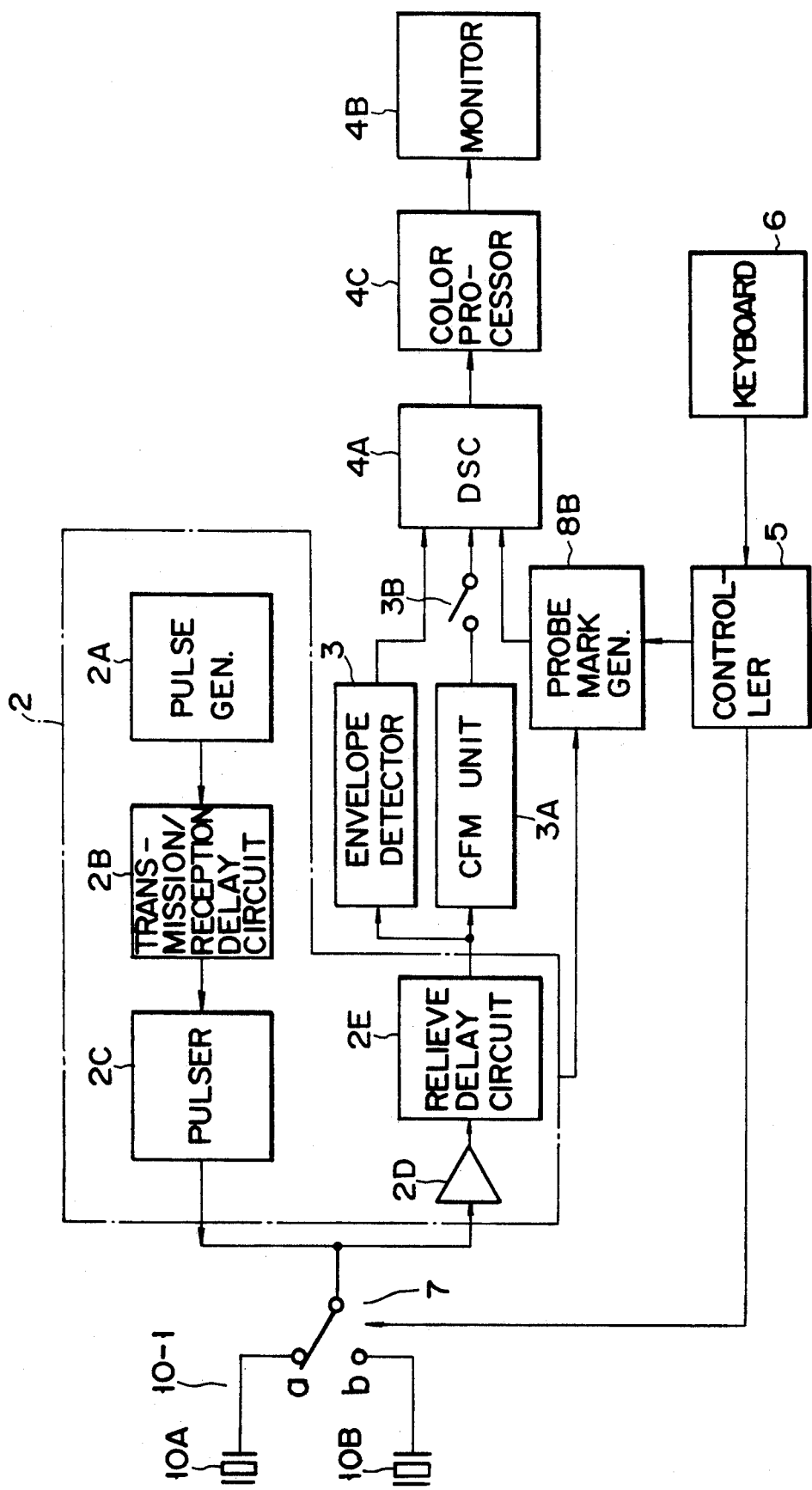
FIG. 16 is a block diagram of an ultrasonic diagnosis apparatus according to a fifth embodiment of the present invention.
Figure 17:
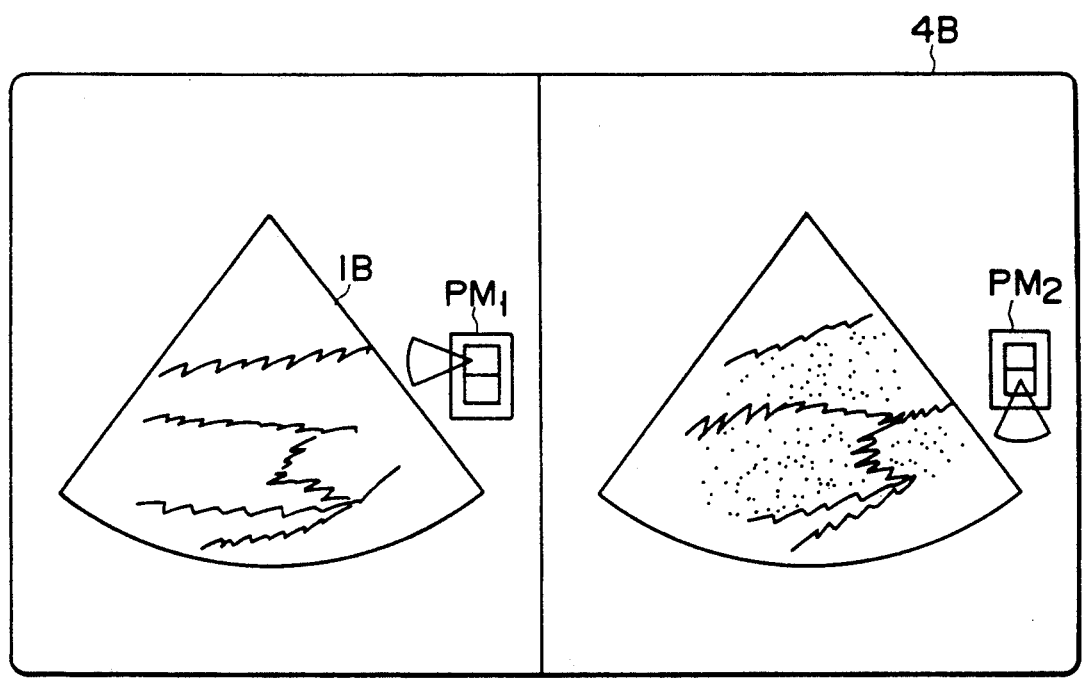
FIG. 17 illustrates a simultaneous display format of a cross-sectional image IB produced by the ultrasonic transducer group 10B, a BDF image IA produced by the ultrasonic transducer group 10A and scanning-plane marks.

A fifth embodiment of the present invention will be described with reference to FIGS. 16 and 17. The fifth embodiment, as shown in FIG. 16, is the same as the embodiment of FIG. 14 except that a probe-mark generator 8B is provided in place of the scanning-plane mark generator 8A in FIG. 14.

With such an arrangement, as in the fourth embodiment, a cross-sectional image can be obtained by the transducer unit 10-1 when the switch 3B is turned OFF, while a BDF image in which a CFM image is superimposed on the cross-sectional image can be obtained by the transducer unit 10-1 when the switch 3B is turned ON. Thus, supposing that, for example, the switch 3B is OFF when the transducer group 10B in the transducer unit 10-1 is selected, while the switch is ON when the transducer group 10A is selected, such a display image as shown in FIG. 17 will be obtained. As shown in FIG. 17, the cross-sectional image IB in the scanning plane B is obtained by the transducer group 10B. The probe mark PM1 is displayed in the neighborhood of the cross-sectional image IB. Also, a BDF image in the scanning plane A is obtained by the transducer group 10A. The probe mark PM2 is displayed in the neighborhood of the BDF image.

Figure 18:
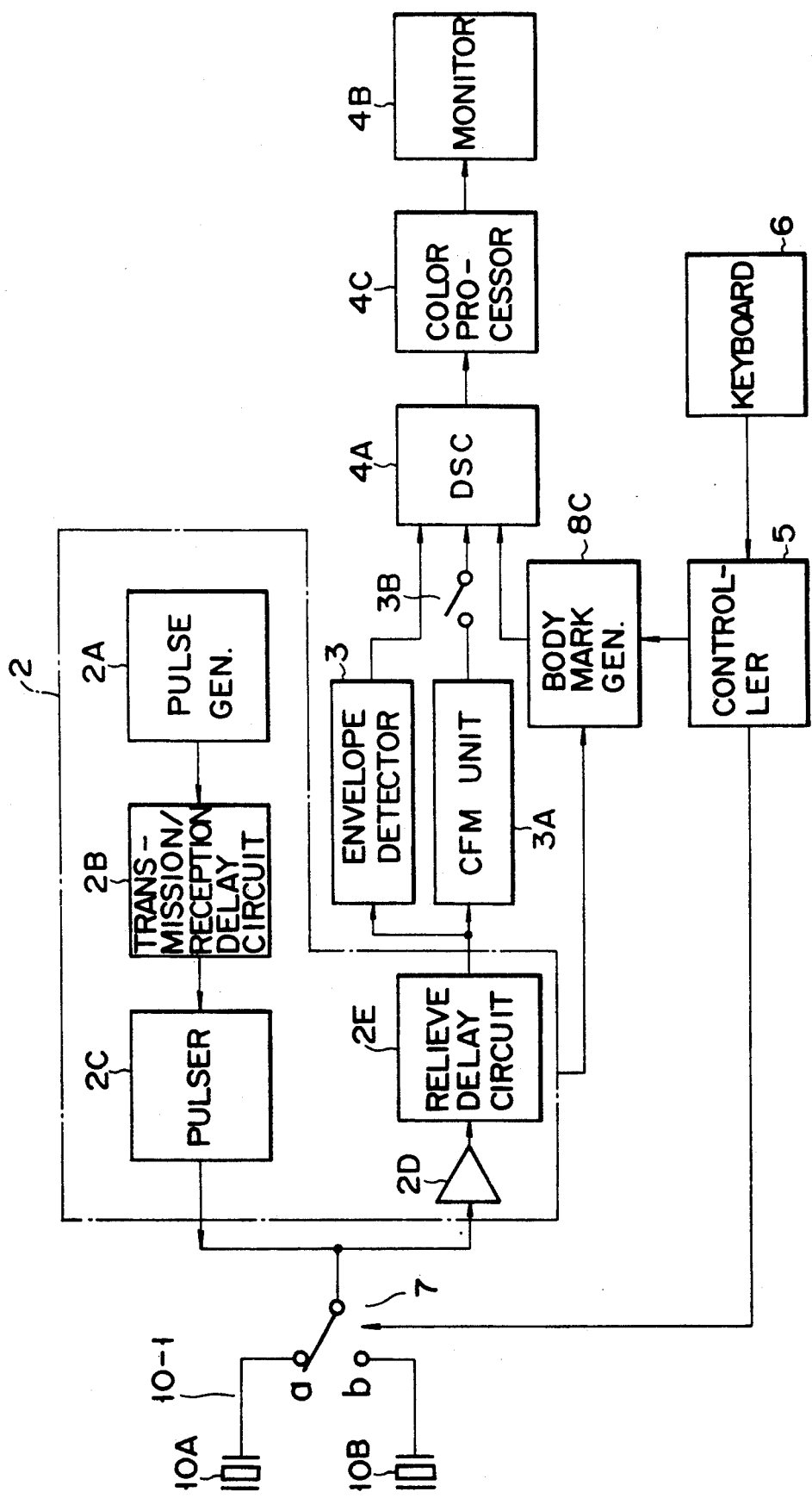
FIG. 18 is a block diagram of an ultrasonic diagnosis apparatus according to a sixth embodiment of the present invention.

A sixth embodiment of the present invention will be described with reference to FIGS. 18 and 19. The sixth embodiment, as shown in FIG. 18, is the same as the embodiment of FIG. 14 except that a body-mark generator 8C is provided in place of the scanning-plane mark generator 8A in FIG. 14.

With such an arrangement, as in the fourth and fifth embodiments, a cross-sectional image can be obtained by the transducer unit 10-1 when the switch 3B is turned OFF, while a BDF image in which a CFM image is superimposed on the cross-sectional image can be obtained by the transducer unit 10-1 when the switch 3B is turned ON. Thus, supposing that, for example, the switch 3B is OFF when the transducer group 10B in the transducer unit 10-1 is selected, while the switch is ON when the transducer group 10A is selected, such a display image as shown in FIG. 19 will be obtained. As shown in FIG. 19, the cross-sectional image IB in the scanning plane B is obtained by the transducer group 10B. The body mark BM1 is displayed in the neighborhood of the cross-sectional image IB. Also, a BDF image in the scanning plane A is obtained by the transducer group 10A. The body mark BM2 is displayed in the neighborhood of the BDF image. The body mark BM indicates the relationship in position on the subject under examination between the scanning plane A formed by the ultrasonic transducer group 10B for the image IB and the scanning plane B formed by the ultrasonic transducer groups 10B for the BDF image by means of an illustration of the subject under examination and/or the ultrasonic probe 10. By making a difference in brightness between one line and the other line of a cross-line mark, the body mark permits an operator to understand which of the ultrasonic transducer groups 1A and 1B is used to produce an ultrasonic image being displayed. In this case, at least one character such as T and L as shown in FIG. 19, is provided in pace of the body mark in FIG. 19. The character T indicate a transverse plane, and the character L indicate a longitudinal plane.

Figure 21:
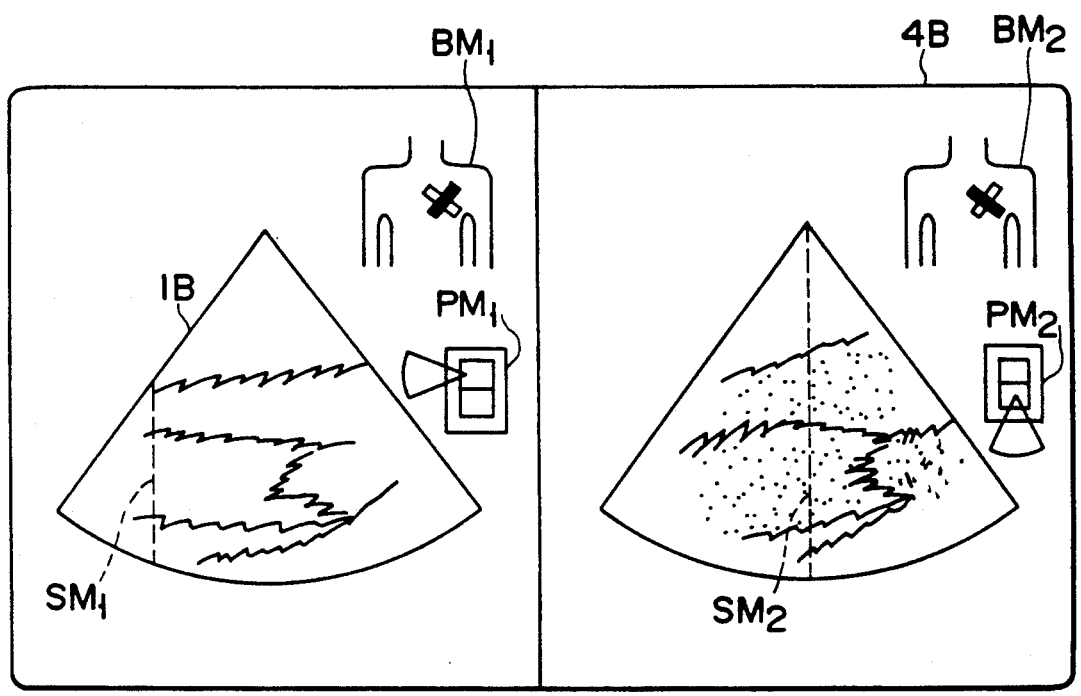
FIG. 21 illustrates a simultaneous display format of a cross-sectional image IB produced by the ultrasonic transducer group 10B, a BDF image produced by the ultrasonic transducer group 10A of the apparatus of FIG. 20, scanning-plane marks, probe marks and body marks.

A seventh embodiment of the present invention will be described with reference to FIGS. 20 and 21. The seventh embodiment, as shown in FIG. 20, is the same as the embodiment of FIG. 14 except that a mark generator 8 is provided in place of the scanning-plane mark generator 8A in FIG. 14. The mark generator 8 can generate a mark in the following modes. In a first mode, the scanning-plane mark SM and the probe mark BM are displayed simultaneously. In a second mode, the scanning-plane mark SM and the body mark BM are displayed simultaneously. In a third pattern, the probe mark BM and the body mark BM are displayed simultaneously. In the fourth mode, the scanning-plane mark SM, the probe mark BM and the body mark BM are displayed simultaneously.

According to such an arrangement, as in the fourth, fifth and sixth embodiments, a cross-sectional image can be obtained by the ultrasonic transducer unit 10-1 when the switch 3B is turned OFF, while a BDF image in which a CFM image is superimposed on the cross-sectional image can be obtained by the ultrasonic transducer unit 10-1 when the switch 3B is turned ON. Thus, supposing that, for example, the switch 3B is OFF when the ultrasonic transducer group 10B in the ultrasonic transducer unit 10-1 is selected and the switch is ON when the ultrasonic transducer group 10A is selected, then such a display image as shown in FIG. 19 will be obtained. FIG. 19 corresponds to the case where the mark generator 8 generates the mark in the fourth mode. As shown in FIG. 19, the cross-sectional image IB in the scanning plane B is obtained by the ultrasonic transducer group 10B. The scanning-plane mark SM1 is displayed on the cross-sectional image IB. The probe mark PM1 is displayed in the neighborhood of the cross-sectional image IB. The BDF image in the scanning plane A is obtained by the ultrasonic transducer group 10A. The scanning-plane mark SM2 is displayed on the BDF image. The probe mark PM2 is displayed in the neighborhood of the BDF image. The body mark BM2 is displayed in the neighborhood of the BDF image.

Figure 22:
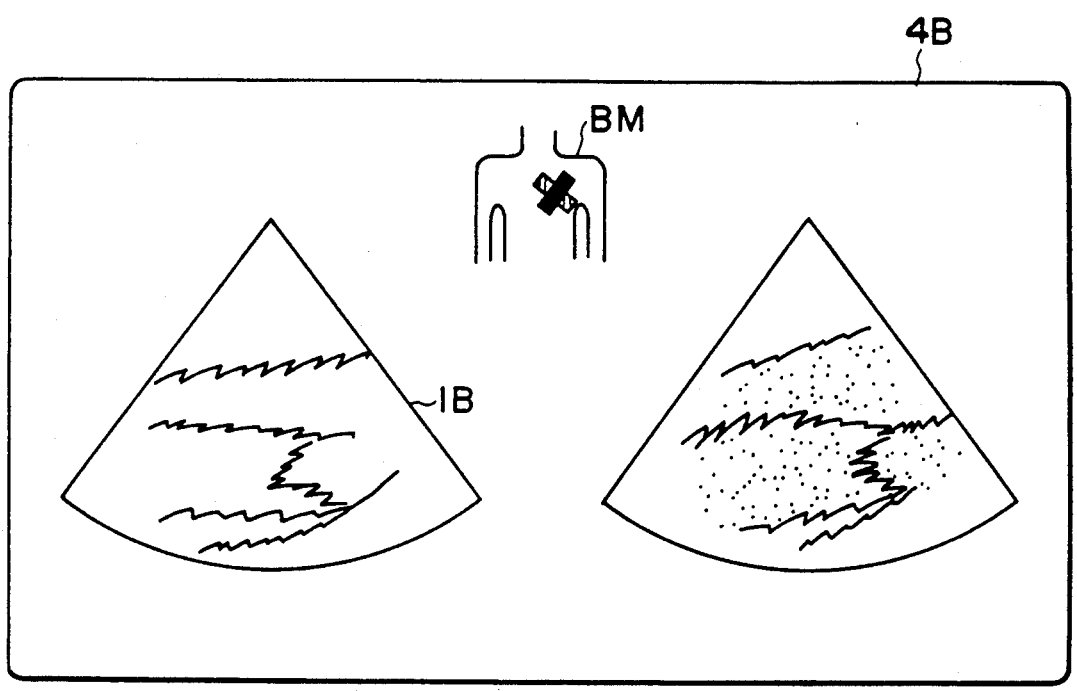
FIG. 22 illustrates another display example of the body mark.

Although, in the arrangement of FIGS. 19 and 20, each of the body marks BM1 and BM2 is displayed in the neighborhood of a corresponding one of the images produced by the ultrasonic transducer groups 1A and 1B, a single body mark BM may be displayed between the images produced by the transducer groups 1A and 1B as shown in FIG. 22. By making a difference in brightness between one line and the other line of the cross-line mark, the body mark permits discrimination between the scanning planes of the ultrasonic cross-sectional images by the ultrasonic transducers groups 1A and 1B. In the example of FIG. 22, a line at a black level and a line at a gray level are crossed. The black line indicates the scanning plane of the image produced by the ultrasonic transducer group 1B, while the gray line indicates the scanning plane of the image produced by the ultrasonic transducer group 1A.

Although, in the embodiments described above, an ultrasonic transducer unit comprising two ultrasonic transducers, which is what is referred to as a biplane probe, is used, the present invention may be applied to the case where more than two ultrasonic transducers are used to display ultrasonic cross-sectional images in more than two scanning planes.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic diagnosis apparatus comprising:
   an ultrasonic probe having a plurality of ultrasonic transducer groups, each transducer group comprising a plurality of ultrasonic transducer elements and said transducer groups having different directions of arrangement of the ultrasonic transducer elements to form different ultrasonic scanning planes;
   selecting means for selecting at least one of said ultrasonic transducer groups;
   driving means for driving at least one of said ultrasonic transducer groups selected by said selecting means to transmit and receive ultrasonic waves;
   ultrasonic-image producing means responsive to a received signal from an ultrasonic transducer group driven by said driving means to produce an ultrasonic image;
   scanning-plane mark generating means for generating a signal corresponding to a scanning-plane mark adapted to indicate the positional relationship between the ultrasonic scanning plane formed by a first ultrasonic transducer group selected by said selecting means and the ultrasonic scanning plane formed by a second ultrasonic transducer group; and
   display means for displaying an ultrasonic image produced by said ultrasonic image producing means and said scanning-plane mark generated by said scanning-plane mark generating means.

2. An ultrasonic diagnosis apparatus according to claim 1, in which said ultrasonic probe is a biplane probe, said biplane probe having two ultrasonic transducer groups, said transducer elements of said transducer groups arranged to form two orthogonal scanning planes.

3. An ultrasonic diagnosis apparatus according to claim 1, in which said ultrasonic probe is an ultrasonic probe adapted for a body cavity.

4. An ultrasonic diagnosis apparatus according to claim 1, in which said ultrasonic probe is an ultrasonic probe adapted for a body surface.

5. An ultrasonic diagnosis apparatus according to claim 1, in which said ultrasonic image producing means includes means for producing an ultrasonic cross-sectional image and/or a BDF image in which a color flow mapping image is superimposed on the ultrasonic cross-sectional image.

6. An ultrasonic diagnosis apparatus according to claim 1, in which said display means includes means for displaying a superimposition image in which said scanning-plane mark generated by said scanning-plane mark generating means is superimposed on the ultrasonic image produced by said image producing means.

7. An ultrasonic diagnosis apparatus according to claim 1, in which said display means includes means for displaying ultrasonic images in a plurality of scanning planes and a scanning-plane mark for each of said ultrasonic images.

8. An ultrasonic diagnosis apparatus according to claim 1, in which said scanning plane mark indicates a cross-line of the ultrasonic scanning plane formed by a first ultrasonic transducer group selected by said selecting means and an ultrasonic scanning plane formed by a second ultrasonic transducer group.

9. An ultrasonic diagnosis apparatus according to claim 8, in which said cross-line is superimposed on said ultrasonic image produced by said ultrasonic image producing means.

10. An ultrasonic diagnosis apparatus comprising:
    an ultrasonic probe having a plurality of ultrasonic transducer groups, each transducer group comprising a plurality of ultrasonic transducer elements and said transducer groups having different directions of arrangement of the ultrasonic transducer elements to form different ultrasonic scanning planes;
    selecting means for selecting at least one of said ultrasonic transducer groups;
    driving means for driving at least one of said ultrasonic transducer groups selected by said selecting means to transmit and receive ultrasonic waves;
    ultrasonic-image producing means responsive to a received signal from an ultrasonic transducer group driven by said driving means to produce an ultrasonic image;
    probe mark generating means for generating a signal corresponding to a probe mark adapted to indicate the positional relationship between the ultrasonic scanning plane formed by a first ultrasonic transducer group selected by said selecting means and an ultrasonic scanning plane formed by a second ultrasonic transducer group, said probe mark corresponding to an illustration of said ultrasonic probe; and display means for displaying an ultrasonic image produced by said ultrasonic image producing means and said probe mark generated by said probe mark generating means.

11. An ultrasonic diagnosis apparatus according to claim 10, in which said ultrasonic probe is a biplane probe, said biplane probe having two ultrasonic transducer groups, said transducer elements of said transducer groups arranged to form two orthogonal scanning planes.

12. An ultrasonic diagnosis apparatus according to claim 10, in which said ultrasonic probe is an ultrasonic probe adapted for a body cavity.

13. An ultrasonic diagnosis apparatus according to claim 10, in which said ultrasonic probe is an ultrasonic probe adapted for a body surface.

14. An ultrasonic diagnosis apparatus according to claim 10, in which said ultrasonic image producing means includes means for producing an ultrasonic cross-sectional image and/or a BDF image in which a color flow mapping image is superimposed on said ultrasonic cross-sectional image.

15. An ultrasonic diagnosis apparatus according to claim 10, in which said display means includes means for displaying ultrasonic images in a plurality of scanning planes and a probe mark for each of said ultrasonic images.

16. An ultrasonic diagnosis apparatus comprising:

an ultrasonic probe having a plurality of ultrasonic transducer groups, each transducer group comprising a plurality of ultrasonic transducer elements and said transducer groups having different directions of arrangement of the ultrasonic transducer elements to form different ultrasonic scanning planes;

selecting means for selecting at least one of said ultrasonic transducer groups;

driving means for driving at least one of said ultrasonic transducer groups selected by said selecting means to transmit and receive ultrasonic waves;

ultrasonic-image producing means responsive to a received signal from an ultrasonic transducer group driven by said driving means to produce an ultrasonic image;

body mark generating means for generating a signal corresponding to a body mark adapted to indicate the relationship in position between the ultrasonic scanning plane formed by a first ultrasonic transducer group selected by said selecting means and an ultrasonic scanning plane formed by a second ultrasonic transducer group, said body mark corresponding to an illustration of an ultrasonic probe on a subject under examination; and display means for displaying an ultrasonic image produced by said ultrasonic image producing means and said body mark generated by said body mark generating means.

17. An ultrasonic diagnosis apparatus according to claim 16, in which said ultrasonic probe is a biplane probe, said biplane probe having two ultrasonic transducer groups, said transducer elements of said transducer groups arranged to form two orthogonal scanning planes.

18. An ultrasonic diagnosis apparatus according to claim 16, in which said ultrasonic probe is an ultrasonic probe adapted for a body cavity.

19. An ultrasonic diagnosis apparatus according to claim 16, in which said ultrasonic probe is an ultrasonic probe adapted for a body surface.

20. An ultrasonic diagnosis apparatus according to claim 16, in which said ultrasonic image producing means includes means for producing at least one of an ultrasonic cross-sectional image and a BDF image in which a color flow mapping image is superimposed on said ultrasonic cross-sectional image.

21. An ultrasonic diagnosis apparatus according to claim 16, in which said display means includes means for displaying ultrasonic images in a plurality of scanning planes and a probe mark for each of said ultrasonic images.

22. An ultrasonic diagnosis apparatus comprising:

an ultrasonic probe having a plurality of ultrasonic transducer groups, each transducer group comprising a plurality of ultrasonic transducer elements and said transducer groups having different directions of arrangement of the ultrasonic transducer elements to form different ultrasonic scanning planes;

selecting means for selecting at least one of said ultrasonic transducer groups;

driving means for driving at least one of said ultrasonic transducer groups selected by said selecting means to transmit and receive ultrasonic waves;

ultrasonic-image producing means responsive to a received signal from an ultrasonic transducer group driven by said driving means to produce an ultrasonic image;

mark generating means for generating at least one of: a scanning-plane mark adapted to indicate the positional relationship between an ultrasonic scanning plane formed by a first ultrasonic transducer group selected by said selecting means and an ultrasonic scanning plane formed by a second ultrasonic transducer group; a probe mark adapted to indicate the positional relationship between an ultrasonic scanning plane formed by a first ultrasonic transducer group selected by said selecting means and an ultrasonic scanning plane formed by a second ultrasonic transducer group corresponding to an illustration of said ultrasonic probe; a body mark adapted to indicate the positional relationship between an ultrasonic scanning plane formed by a first ultrasonic transducer group selected by said selecting means and an ultrasonic scanning plane formed by a second ultrasonic transducer group corresponding to an illustration of an ultrasonic probe on said subject under examination; and character information adapted to indicate the positional relationship between an ultrasonic scanning plane formed by a first ultrasonic transducer group selected by said selecting means and an ultrasonic scanning plane formed by a second ultrasonic transducer group; and display means for displaying an ultrasonic image produced by said ultrasonic image producing means and said marks generated by said mark generating means.

23. An ultrasonic diagnosis apparatus according to claim 22, in which said ultrasonic probe is a biplane probe, said biplane probe having two ultrasonic transducer groups, said transducer elements of said transducer groups arranged to form two orthogonal scanning planes.

24. An ultrasonic diagnosis apparatus according to claim 22, in which said ultrasonic probe is an ultrasonic probe adapted for a body cavity.

25. An ultrasonic diagnosis apparatus according to claim 22, in which said ultrasonic probe is an ultrasonic probe adapted for a body surface.

26. An ultrasonic diagnosis apparatus according to claim 22, in which said ultrasonic image producing means includes means for producing an ultrasonic cross-sectional image and/or a BDF image in which a color flow mapping image is superimposed on said ultrasonic cross-sectional image.

27. An ultrasonic diagnosis apparatus according to claim 22, in which said display means includes means for displaying ultrasonic images in a plurality of scanning planes and said probe mark for each of said ultrasonic images.

28. An ultrasonic diagnosis apparatus comprising:
an ultrasonic probe having a plurality of ultrasonic transducer groups, each transducer group comprising a plurality of ultrasonic transducer elements and said transducer groups having different directions of arrangement of the ultrasonic transducer elements to form different ultrasonic scanning planes;
selecting means for selecting at least one of said ultrasonic transducer groups;
driving means for driving at least one of said ultrasonic transducer groups selected by said selecting means to transmit and receive ultrasonic waves;
ultrasonic-image producing means responsive to a received signal from an ultrasonic transducer group driven by said driving means to produce an ultrasonic image;
character information generating means for generating character information adapted to indicate the positional relationship between an ultrasonic scanning plane formed by a first ultrasonic transducer group selected by said selecting means and the ultrasonic scanning plane formed by a second ultrasonic transducer group; and
display means for displaying an ultrasonic image produced by said ultrasonic image producing means and said character information generated by said character information generating means.

29. An ultrasonic diagnosis apparatus according to claim 28, in which said ultrasonic probe is a biplane probe, said biplane probe having two ultrasonic transducer groups, said transducer elements of said transducer groups arranged to form two orthogonal scanning planes.

* * * * *